United States Patent
Tremulis et al.

(10) Patent No.: US 7,125,421 B2
(45) Date of Patent: Oct. 24, 2006

(54) METHOD AND APPARATUS FOR VALVE REPAIR

(75) Inventors: William S. Tremulis, Redwood City, CA (US); Mahmood K. Razavi, San Carlos, CA (US)

(73) Assignee: Mitral Interventions, Inc., Redwood City, CA (US)

( * ) Notice: Subject to any disclaimer, the term of this patent is extended or adjusted under 35 U.S.C. 154(b) by 0 days.

(21) Appl. No.: 10/232,753

(22) Filed: Aug. 30, 2002

(65) Prior Publication Data

US 2003/0069593 A1    Apr. 10, 2003

Related U.S. Application Data

(60) Provisional application No. 60/388,250, filed on Jun. 12, 2002, provisional application No. 60/316,892, filed on Aug. 31, 2001.

(51) Int. Cl.
*A61F 2/24* (2006.01)
(52) U.S. Cl. ..................................... 623/2.37
(58) Field of Classification Search ............... 623/2.1, 623/2.37, 2.36
See application file for complete search history.

(56) References Cited

U.S. PATENT DOCUMENTS

| | | | | |
|---|---|---|---|---|
| 4,042,979 A * | 8/1977 | Angell | ...................... | 623/2.37 |
| 4,917,698 A * | 4/1990 | Carpentier et al. | ......... | 623/2.36 |
| 5,441,517 A | 8/1995 | Kensey et al. | ............... | 606/213 |
| 5,477,864 A | 12/1995 | Davidson | ..................... | 128/772 |
| 5,584,879 A * | 12/1996 | Reimold et al. | ............ | 623/2.36 |
| 5,716,397 A | 2/1998 | Myers | ............................. | 623/2 |
| 5,871,501 A | 2/1999 | Leschinsky et al. | ........ | 606/213 |
| 5,876,373 A | 3/1999 | Giba et al. | ..................... | 604/95 |
| 6,165,183 A | 12/2000 | Kuehn et al. | ................ | 606/139 |
| 6,183,512 B1 | 2/2001 | Howanec, Jr. et al. | ...... | 623/2.36 |
| 6,290,674 B1 | 9/2001 | Roue et al. | ................... | 604/107 |
| 6,312,447 B1 | 11/2001 | Grimes | .......................... | 606/219 |
| 6,402,736 B1 * | 6/2002 | Brown et al. | ................ | 604/523 |
| 6,402,781 B1 | 6/2002 | Langberg et al. | ........... | 623/2.36 |
| 6,416,548 B1 * | 7/2002 | Chinn et al. | ................ | 623/2.36 |
| 6,419,696 B1 * | 7/2002 | Ortiz et al. | ................. | 623/2.37 |
| 6,595,911 B1 | 7/2003 | LoVuolo | ....................... | 600/30 |
| 6,602,288 B1 * | 8/2003 | Cosgrove et al. | ........... | 623/2.36 |
| 6,651,672 B1 * | 11/2003 | Roth | ........................... | 128/898 |
| 6,656,178 B1 * | 12/2003 | Veldhuizen et al. | ........... | 606/61 |
| 2002/0151961 A1 * | 10/2002 | Lashinski et al. | ........... | 623/1.15 |

FOREIGN PATENT DOCUMENTS

| | | |
|---|---|---|
| EP | 0257874 | 3/1988 |
| EP | 0595791 | 5/1994 |
| EP | 1088529 | 4/2001 |
| FR | 2799364 | 10/1999 |
| WO | WO97/03625 | 2/1997 |

(Continued)

*Primary Examiner*—Corrine McDermott
*Assistant Examiner*—William H Matthews
(74) *Attorney, Agent, or Firm*—Paul Davis; Heller Ehrman LLP

(57) ABSTRACT

A tissue connection device is provided for use on a patient at a treatment site. The device comprises an elongate member having a distal end and a proximal end. The elongate member has a first, substantially linear configuration during delivery through an elongate delivery device, wherein the first configuration is sufficient to allow said member to be delivered percutaneously into the patient to the treatment site. The elongate member has a second, substantially circular configuration when said member disengages from the delivery device, wherein the second configuration is sufficient to support tissue at the treatment site. The elongate member in the second configuration defines a single ring.

79 Claims, 13 Drawing Sheets

FOREIGN PATENT DOCUMENTS

| WO | WO02/03892 | 1/2002 |
| WO | WO02/28321 | 4/2002 |

* cited by examiner

Valve Leaflets

METHOD AND APPARATUS FOR VALVE REPAIR

The present application claims the benefit of priority from commonly assigned, co-pending U.S. Provisional Patent Application Ser. No. 60/316,892 filed Aug. 31, 2001 and U.S. Provisional Patent Application Ser. No. 60/388,250 filed Jun. 12, 2002. The complete disclosure of all applications listed above are incorporated herein by reference for all purposes.

BACKGROUND OF THE INVENTION

1. Field of the Invention

The present invention relates to valve tissue repair or reshaping. More specifically, the present invention relates to minimally invasive devices and methods for repair or reshaping of improperly functioning heart valves.

2. Description of Related Art

The human body has a plurality of valves for regulating fluid flow and, due to disease or genetic abnormality, these valves may become dysfunctional over a patient's lifetime. The majority of these valves are located in the heart, but valve structures are also located in the digestive track above the stomach and at other locations. One of the main problems associated with diseased or dysfunctional valves, particularly in the heart, is undesired valve dilation due to weakening of the valve leaflets or valve support structure. This valve leakage is commonly described as valve regurgitation and may be characterized by retrograde flow of fluid through the valve. In the heart, such valve regurgitation may seriously compromise the pumping efficiency of the heart and, if left unchecked, can result in extreme fatigue and the inability of the patient to lead a normal life.

Various surgical techniques have been developed to repair a diseased or damaged valve. These typical treatments for valve regurgitation or other valve repair involve conventional, open surgical techniques. For repair of coronary valves, the chest of the patient is usually opened, at least in part, to allow enough room for the surgeon to perform a repair or replacement of the damaged valve. This usually requires that the patient be placed on a bypass machine to pump the blood while the surgeon operates on the stopped heart muscle. For obvious reasons, this open-type of surgery can be very traumatic on the patient and recovery may take many months. Additionally, surgery may not be an option for some patients due to limited possibility for recovery, concurrent disease, or age.

For these reasons, it would be desirable to provide an alternative to open-type surgery to modify or repair a damaged valve that minimizes the need for the patient's chest to be opened and/or the patient to be placed on bypass during the procedure

SUMMARY OF THE INVENTION

The present invention provides new and novel devices, methods and systems for the repair of the valves and for their modification and subsequent improvement in valve function. More specifically, in some embodiments, the present invention achieves these repairs using percutaneous endovascular techniques that minimize trauma to the patient and provide reduced recovery time and recovery cost.

In one aspect of the present invention, a tissue connecting device is provided for use with an elongate delivery device on tissue at a target site. The device comprises an elongate member deliverable to the target site via the elongate delivery device, wherein the elongate member assumes a first substantially linear configuration while engaged with said elongate delivery device and a second substantially circular configuration defining a first support ring and a second support ring when removed from the elongate delivery device. The elongate member may have a first support ring radial thickness different from a second support ring radial thickness. The first support ring is configured to abut against one side of the target tissue and the second support ring is configured to abut against an opposite side of the target tissue to thereby capture a portion of the target tissue therebetween. This tissue connection device may be delivered percutaneously into the patient.

In another embodiment of the present invention, a tissue connecting device is provided for use with an elongate delivery device on tissue at a target site. The device comprises an elongate member deliverable to a target site via the elongate delivery device, wherein the elongate member assumes a first substantially linear configuration while in the catheter and a second substantially circular configuration defining a first support ring and a second support ring when removed from the catheter. The second support ring may be shaped to clamp down on the inner circumferential surface of first ring, wherein the clamping by the rings urges tissue radially inward to enable better tissue capture and to lessen dilation of opening in the tissue.

In still another embodiment of the present invention, a tissue connection device is provided for use with an elongate delivery device on tissue at a treatment site in a patient. The device comprises an elongate member deliverable to a target tissue site via the elongate delivery device, wherein the elongate member assuming a first substantially linear configuration while engaged with the elongate delivery device and a second relaxed configuration defining a first support ring and a second support ring when removed from the elongate delivery device. The first support ring may be configured to abut against one side of the target tissue and the second support ring configured to abut against an opposite side of the target tissue to engage said target tissue therebetween. Additionally, the first support ring may be coupled to said second support ring via a portion of the elongate member extending from the first support ring, radially inward towards the center of the first support ring, extending upward, and the radially outward towards the second support ring so as to avoid penetration of valve tissue while the first support ring and second support ring engage target tissue therebetween.

In another embodiment of the present invention, a tissue connection device is provided for use with an elongate delivery device and at least one suture on tissue at a treatment site in a patient. The device comprises an elongate member deliverable to a target tissue site via the elongate delivery device, wherein the elongate member assumes a first substantially linear configuration while engaged with the elongate delivery device and a second relaxed configuration defining a first support ring and a second support ring when removed from the elongate delivery device. The elongate member may have a circular configuration shaped to have a distance between a first ring tissue engaging surface and a second ring tissue engaging surface.

In another embodiment, a tissue connection device is provided for use with a tubular delivery device. The device comprises a central body and a first leaflet clamp coupled to said central body and extending radially outward from the central body and defining an upper compressive portion. The device further comprises a second leaflet clamp coupled to said central body and extending radially outward from the central body and defining a lower compressive portion. The first leaflet clamp and second leaflet clamp coupled to the central body may be deliverable through a tubular delivery device, wherein the first leaflet clamp and second leaflet clamp assume a first folded configuration during delivery to a target site. The leaflets clamps may be deflected towards a longitudinal axis of the central body to provide a reduced diameter. The first leaflet clamp and second leaflet clamp assumes a second, opened configuration having an extended diameter after exiting the tubular delivery device. The first leaflet clamp configured to abut against one side of the target tissue and the second leaflet clamp configured to abut against an opposite side of the target tissue to thereby engage a portion of the target tissue therebetween.

In another embodiment of the present invention, a tissue connection device is provided for use with a tubular delivery device. The device comprises a first clamp portion having a central body with a lumen and at least a first leaflet extending radially away from the central body and a second clamp portion having a spine and at least a second leaflet extending radially away from the spine. The spine of the second clamp portion is configured to slidably engage the lumen on said central body and the spine is shaped to retain said first clamp portion in a position where said first clamp portion abuts against one side of a target tissue and the second clamp portion abuts against an opposite side of the target tissue to thereby engage a portion of the tissue therebetween.

In a still further embodiment, an annuloplasty device is provided for use on a patient at a treatment site. The device comprises an elongate member having a distal end and a proximal end. The elongate member has a first, substantially linear configuration during delivery through a tubular delivery device, wherein the first configuration is sufficient to allow the member to be delivered percutaneously into the patient to the treatment site. The elongate member may have a second, substantially circular configuration when the member exits the tubular delivery device, wherein the second configuration is sufficient to support tissue at the treatment site. Although not limited in this manner, the elongate member in the second configuration may define a single ring.

In another aspect of the present invention, a method for valve repair in a patient's body is provided. The method comprises of directing sutures through target tissue to provide secure anchoring sites at a target tissue site. Sutures may be connected to a tissue connection device, wherein the tissue connection device is slidable over the sutures. An elongate delivery device may be used to percutaneously deliver the tissue connection device to a target tissue site; wherein the tissue connection device having a first, substantially linear configuration when contained in said tubular delivery device and a second, substantially circular configuration when said ring exits said tubular delivery device. The method further comprises delivering the tissue connection device entirely on one side of the treatment site.

In another embodiment of the present invention, a method is provided for repairing a tissue valve having an annulus and a plurality of valve leaflets. The method comprises positioning an elongate delivery device between the valve leaflets without penetrating valve tissue to provide access to first side of the valve to percutaneously deliver a first portion of the tissue connection device to a target tissue site. The method further includes withdrawing the delivery device from between the leaflets to the opposite side of the tissue to continue delivery of the remaining portion of the tissue connection device on the opposite side thereby engaging the leaflets therebetween. The tissue connection device may have a first, substantially linear configuration when engaged with the delivery device and a second, substantially circular configuration when the member exits the delivery device.

In another aspect of the present invention, a method is provided for repairing a tissue valve having an annulus and a plurality of valve leaflets. The method comprises positioning an elongate delivery device to provide access to first side of the valve to percutaneously deliver a first portion of the tissue connection device to a target tissue site. The method further includes withdrawing the delivery device from between the leaflets to the opposite side of the tissue to continue delivery of the remaining portion of the tissue connection device on the opposite side, wherein the first portion and the portion on the opposite side are substantially spaced apart. The tissue connection device may have a first, substantially linear configuration when contained in the delivery device and a second, substantially circular configuration when said member exits the delivery device. The method may further include using at least one suture to draw the first portion and the second portion together to compress tissue therebetween.

In another embodiment of the present invention, a method is provided for repairing a tissue valve having an annulus and a plurality of valve leaflets. The method comprises positioning a first tubular delivery device on one side of the tissue valve to deliver a first support member to a target tissue site. The method further comprises positioning a second tubular delivery device on an opposite side of the tissue valve to deliver a second support member to a target tissue site. A guide wire may be extended outward from the first tubular delivery device, past the tissue valve, and into the second tubular delivery device to provide for alignment between the first tubular delivery device and second tubular delivery device. .

In a still further aspect of the present invention, a kit is provided for delivering a tissue connection device to a valve having an annulus and a plurality of leaflets. The kit may include an elongate member having a first substantially linear configuration when engaged with an elongate delivery device and a second substantially circular configuration defining a first support ring and a second support ring when the member disengages from the delivery device. The kit may further include instructions for use describing a method for connecting the elongate member to the valve and a package for holding the elongate member and the instructions for use.

A further understanding of the nature and advantages of the invention will become apparent by reference to the remaining portions of the specification and drawings.

DETAILED DESCRIPTION

The present invention provides new and novel devices, methods and systems for the repair of a valve and for their modification and subsequent improvement in valve function. More specifically, in some embodiments, the present invention achieves these repairs using percutaneous endovascular techniques that minimize trauma to the patient and provide reduced recovery time and cost. One particularly useful and immediate benefit for these devices, methods and systems is in the bringing together, or coaptation, of heart valve leaflets so that they close properly against the relatively high pressures during the contraction of the heart muscle so as to improve the pumping efficiency of the heart muscle.

Figure 1:
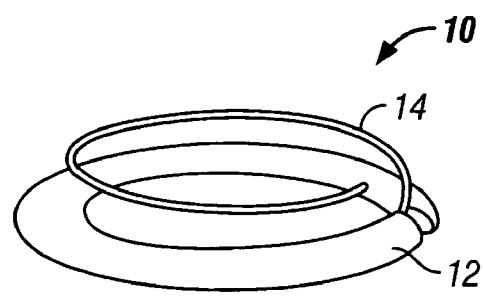
FIG. 1 is perspective view of an annular support device.

Referring now to FIG. 1, in one embodiment of the present invention, a tissue connection device 10 suitable for minimally invasive delivery comprises a first support ring or annular support ring 12 and a second support ring or attached clamp 14 that secures the ring 12 to the opposite sides of the valve tissue. The first support ring 12 provides support for the annular ring of tissue surrounding the heart valve or other target site so that proper coaptation may occur with the valve leaflets (see FIG. 5). As seen in the embodiment of FIG. 1, the first support ring 12 may be substantially in a first plane while the second support ring 14 may be substantially in a second plane roughly parallel to the first plane.

Figure 2:
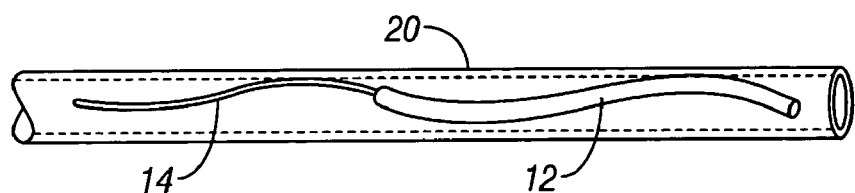
FIGS. 2–5 illustrate the delivery of the device of FIG. 1 to a treatment site.

Referring now to FIG. 2, delivery of the device 10 may be accomplished by straightening the first support ring 12 and second support ring or clamp 14 and inserting device 10 through an elongate delivery device 20 such as, but not limited to, a guide catheter that may be used to access the chambers of the heart. As seen in FIG. 2, the device 10 is an elongate member that assumes a substantially linear configuration when placed inside an appropriately sized guide catheter. In one embodiment, the guide catheter may be sized between about 3 and 15 French (1 mm to 5 mm diameter). When the device 10 is removed from the delivery device 20, the tissue connection device 10 may assume a coiled configuration as shown in FIG. 1.

Figure 3:
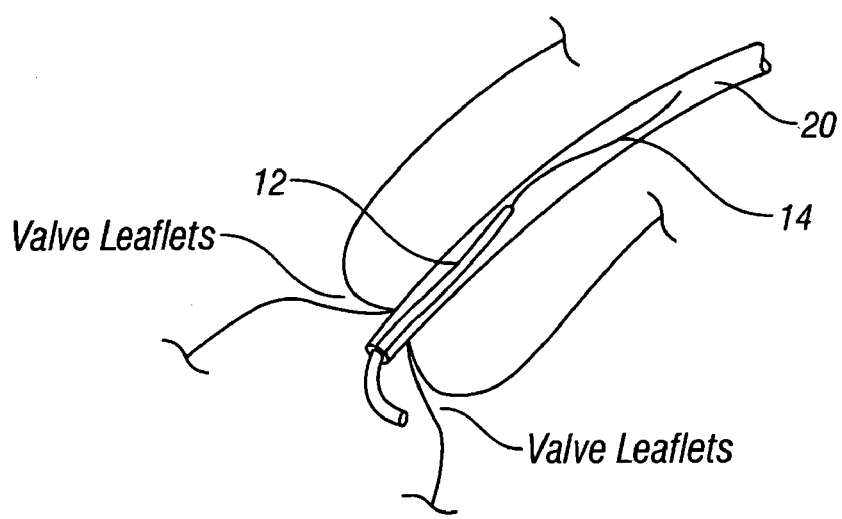

Referring now to FIG. 3, the delivery device 20 such as a guide catheter may be inserted at a location remote from the heart such as the femoral artery, brachial artery, inferior vena cava, jugular vein, etc. In this example, delivery device 20 is then advanced through the vessel to the heart and across the target valve. As the device 10 in a straightened ring or linear configuration is advanced out the distal end of the catheter, the device 10 begins to regain its pre-formed coil or circular shape.

Figure 4:
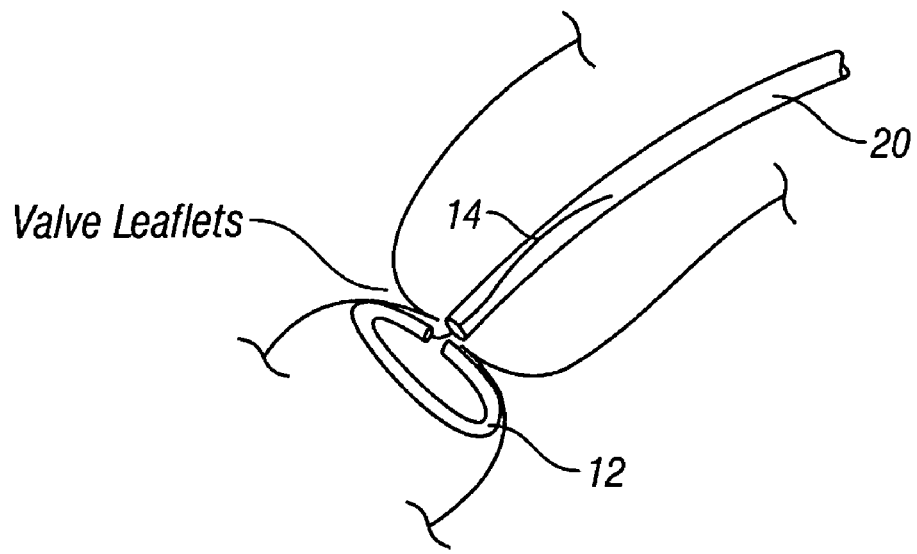

Referring now to FIG. 4, following deployment of the first support ring 12, the delivery device 20 is pulled back to the proximal side of the valve where the clamp portion or second support ring 14 of the device 10 is deployed.

Figure 5:
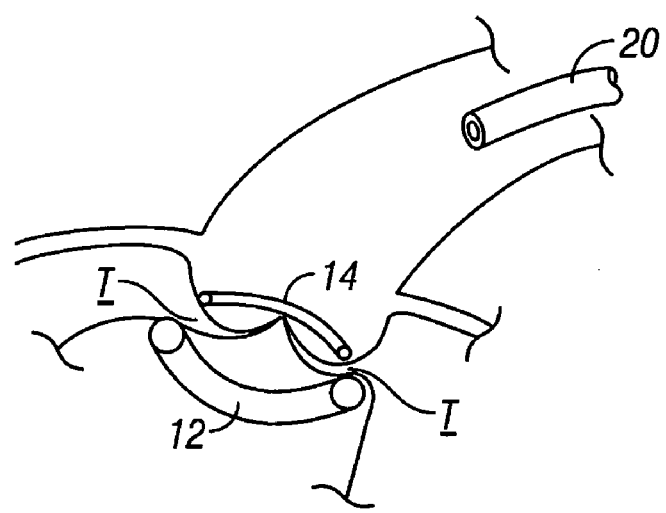

As seen in FIG. 5, the tissue connection device 10 when deployed in the heart valve captures a tissue T between the first support ring 12 and the second support ring 14. The clamping action of device 10 reduces the dilation of the valve formed by tissue T, thus urging the leaflets closer to the center of the valve. It should be understood that, in some embodiments, configuration may be reversed where the second support ring 14 is on the bottom of the valve and the first support ring 12 is located on top. Furthermore, as seen in FIGS. 1–5, the first support ring 12 may be thicker or have a greater radial thickness than the radial thickness of the second support ring 14. The greater radial thickness may provide improved support or capture to tissue engaged between the rings. Additionally, the second support ring 14 having a smaller radial thickness may be more easily situated on sides of the valve with chordae or other materials that may interfere with proper device seating. Still further, as discussed for FIGS. 7A and 7B, the varying thicknesses may also provide a desired reshaping of tissue captured between the rings 12 and 14 to reduce dilation of the valve tissue.

Figure 6:
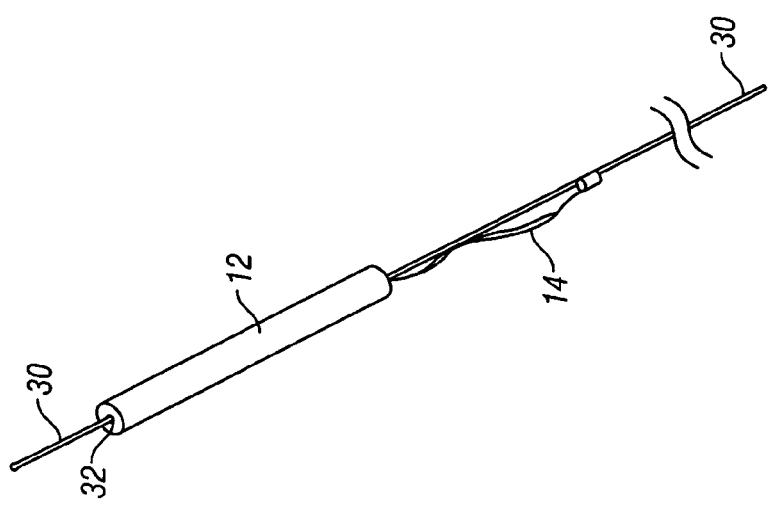
FIG. 6 shows another embodiment of present invention for use with a straightening mandrel.

Referring now to FIG. 6, in another embodiment of the present invention, the device 10 may be configured for use with a straightening mandrel 30 that is used as a delivery device 20 to deploy the device 10 to the target site. As seen in FIG. 6, the straightening mandrel 30 may pass through a lumen 32 in the first support ring 12 and a guide loop on the second support ring 14. Thus in this embodiment, the tissue connection device is constrained through internal straightening parts instead of externally constraining parts when a guide catheter is used. The device 10 is loaded onto a straightening mandrel 30 or guide wire for delivery and upon removal of the mandrel or guide wire, the annuloplasty ring and/or clamp reverts back to its pre-determined remembered shape, typically in its valve supportive configuration. The hollow device 10 and its removable straightening guide wire/mandrel are also adaptable for use with each of the other designs described within this specification, and is not limited to just the annuloplasty ring and clamp configurations.

Figure 7A:
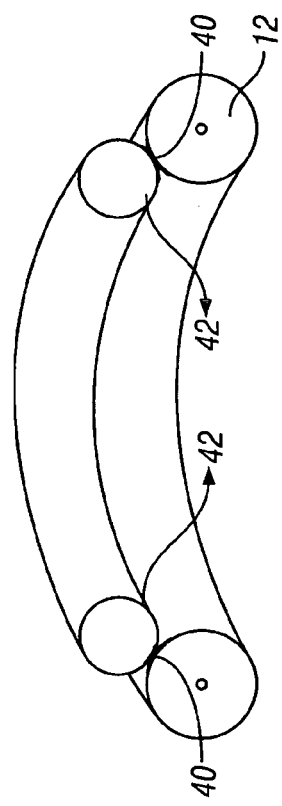
FIGS. 7A and 7B show cross-sectional views of interaction between two support rings to engage tissue therebetween.
Figure 7B:
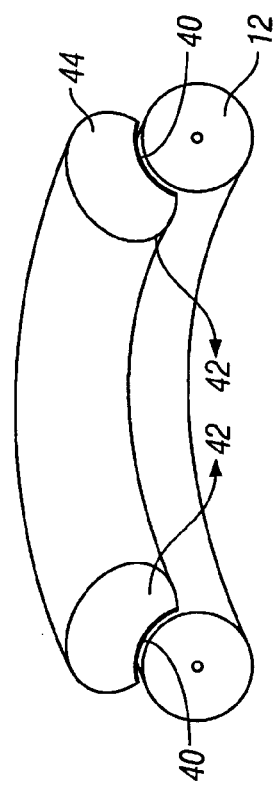

Referring now to FIGS. 7A and 7B, another embodiment of the present invention will now be described. For ease of illustration, the rings are shown to be touching. It should be understood that tissue may be engaged between the rings and captured therebetween. In the embodiment of FIG. 7A, the first support ring 12 has a larger circumference than the second support ring 14. The ring 14 engages an inner circumferential surface 40 of the first support ring 12. This provides a radially inward force as indicated by arrows 42 on an tissue captured between the rings. The outer ring, in this case first support ring 12, may engage the tissue first and then the second ring 14 will engage the tissue and pull it inward. For heart valve reshaping, this will bring the valve leaflets closer to the center and reduce dilation of the valve minimize leakage and regurgitation.

FIG. 7B shows another embodiment where the ring 44 has substantially the same diameter or circumference as the first support ring 12. The ring 44, however, has a cross-sectional geometry wherein the ring 44 only engages the inner circumferential surface 40 of the first support ring 12. Again, the rings will draw tissue radially inward as indicated by arrows 42.

Figure 8A:
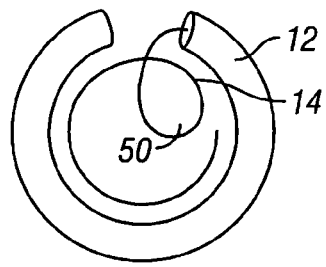
FIGS. 8A and 8B are top and side views of another annular support device.
Figure 8B:
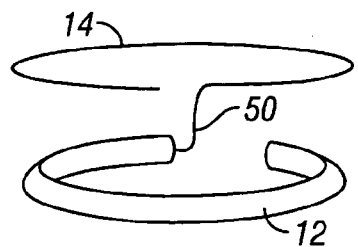

Referring now to FIGS. 8A and 8B, the connection between the support ring 12 and the clamping ring 14 may have variations depending on the valve anatomy, location, and disease condition. For instance in one embodiment, it may be desired to have the connection between the two structures in the center of the valve such that there is no interference with the movement of the valve leaflets (FIGS. 8A and 8B). A portion 50 of the tissue connection device will be configured to extend through the center of the valves.

Figure 9:
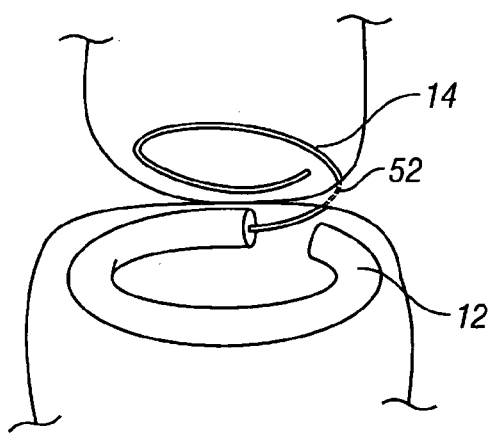
FIG. 9 shows the device of FIG. 1 penetrating tissue.

Referring now to FIG. 9, an alternative embodiment of the present invention has a portion 52 of the elongate member that transverses through the leaflet tissue towards its most outer edge where there would be little or no interference with the valve leaflet. Additionally, this position for the connection would allow the entire device to remain out of the flow of blood through the valve opening. This would have the advantage of no disruption of blood flow through the valve and minimizes bloodstream turbulence and the potential formation and/or dislocation of blood clots around the device.

Figure 10A:
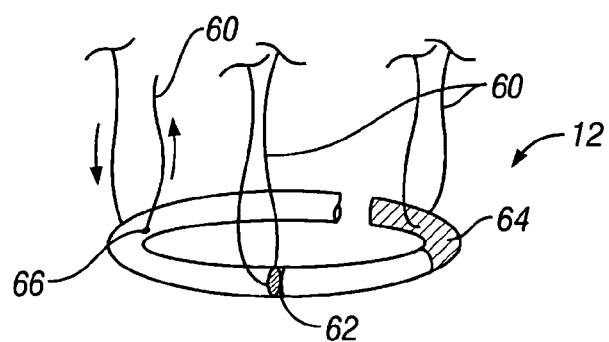
FIGS. 10A–10C show the use of sutures on annular support rings in accordance to the present invention.
Figure 10B:
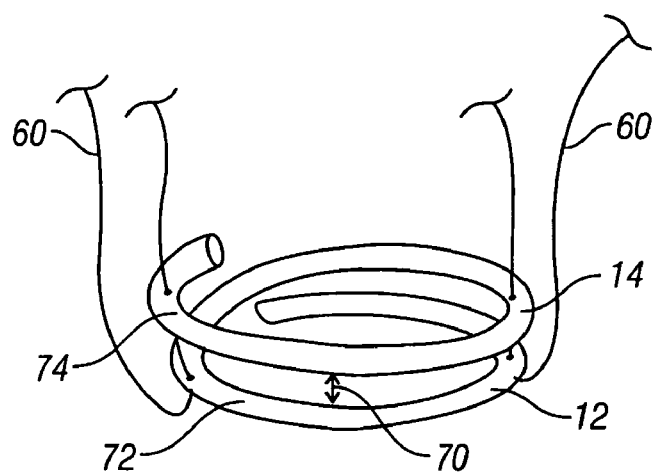
Figure 10C:
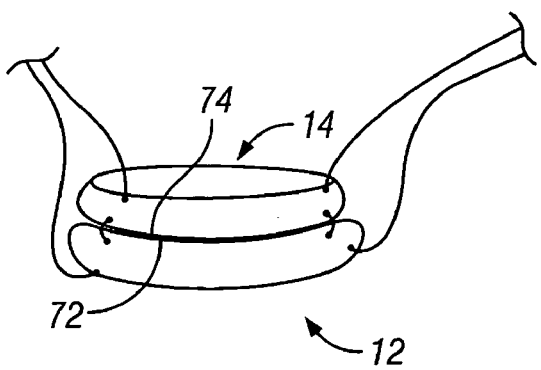

Referring now to FIGS. 10A through 10C, to aid in the proper seating or apposition of the valve annular support structure against the valve tissue, detachable threads or sutures may be attached at various points around the device. As seen in FIG. 10A following deployment of the distal structure, whether first support ring 12 or second support 14, the threads or sutures 60 may be pulled proximally towards the guide catheter, thereby properly seating the structure to the underside of the valve. At least one thread or suture 60 would aid in proper seating, preferably three, so that the orientation of the structure could be adjusted against the valve. The location of each thread or suture 60 on the structure may be identified with unique radiopaque markers 62 to help in the choice of which part of the structure and which corresponding thread needs additional tension for optimum valve support. After positioning the device 10 but before permanent deployment, the improvement in valve function may be assessed. Valve function may be assessed by any suitable means such as angiography, magnetic resonance imaging, ultrasound imaging, trans-esophageal echocardiography and the like. Following verification of improved valve function, one end of the releasable thread could be pulled, removing the thread from its connection to the valve support structure.

Materials used in the construction of the annular support ring 12 or the second support ring/clamping device 14 include, but are not limited to, Nitinol, superelastic metallic alloys and plastics, PTFE, silicone, stainless steel, ceramics and/or other suitable materials or combinations thereof. Additionally, shape-memory alloys and plastics may be used for the support structure and/or the clamping structure in order for the device to be delivered in a straightened condition and, when heated to a temperature above its transition temperature, the valve support structure and/or the clamping structure assume their predetermined geometries. In one embodiment, the temperature of the body would be sufficient to transform the shape of the shape-memory material into its ring and clamp configuration. In another embodiment, energy is applied to the device using electrical, radio frequency, microwave, heated solutions passed through the guide catheter, or other suitable energy source to transform the shape-memory material to its remembered clamping and support shape. Still further, the exterior surface of the first support ring 12 or second support ring 14 may be conditioned to accept penetration or engagement with a needle carrying a suture. As seen in FIG. 10A, the surface may have a mesh or other covering 64 to facilitate coupling with sutures 60. The mesh may be made of a variety of materials such as Dacron® or other suitable material. For ease of illustration, only a portion of the ring 12 is shown to be covered with mesh, though it should be understood that the entire ring may be covered with mesh. Other methods may also be used to facilitate such eyelets, apertures 66, anchoring locations, or connection devices on the ring 12. The ring 12 may also be made entirely of a penetrable material so that sutures may be easily placed in the device. The ring material may also be made porous in order to promote endothelialization of the ring around the valve. A more secure device may aid in the support the implantable ring provides to the valve tissues. Suitable materials for the ring include Nitinol, ceramics, and plastic polymers. Additionally the materials used may elude drugs that may assist in the promotion of endothelialization. Alternatively, the ring may be surrounded by materials such as polyester that promotes tissue ingrowth and endothelialization of the device.

Referring now to FIG. 10B, in another embodiment of the device 10, sutures 60 may be secured to both the first support ring 12 and the second support ring 14 such that, when in its desired position, the sutures apply additional force to the rings 12 and 14 in order to increase the clamping force between the two structures and provide additional support to the valve's annular ring. When delivered, the first support ring 12 and second support ring 14 are spaced apart by a distance 70, wherein a first ring tissue engaging surface 72 is separated from a second ring tissue engaging surface 74.

To secure the clamp section 14 and the support section 12 together, a knot and/or a clamp (or alternate securing means) for each suture 60 is advanced from outside the body, through a guide catheter, and to the device using any one of several knot-tying techniques and/or tools commonly used in vessel closure devices. Additionally, a portion of the suture material 60 may be elastic in order to provide a constant force to the support structure so that during the normal contractions of the heart, the device 10 is allowed limited movement relative to the valve. As seen in FIG. 10C, the device 10 when sutured together may engage tissue captured between surfaces 72 and 74 to reform the valve tissue as desired.

Figure 11:
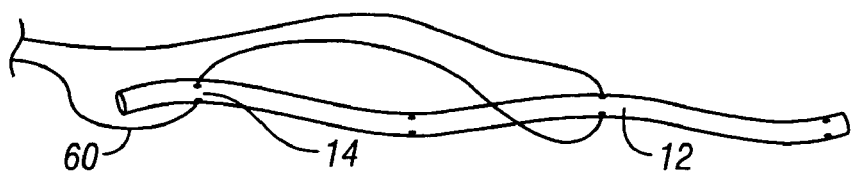
FIG. 11 shows the attachment of sutures to a support ring in a linear configuration.

Referring now to FIG. 11, the device 10 as delivered through a guide catheter 20 with sutures attached, would look similar to the referenced illustration. Each of the pre-threaded sutures 60 attached to the ring structure 12 line up with the corresponding points on the clamp 14 that are located immediately adjacent to the ring attachment points when in its delivered configuration. This facilitates placement and clamping of the device 10.

Figure 12:
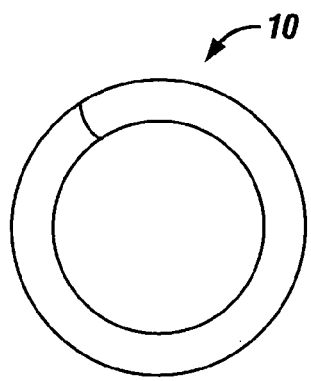
FIGS. 12–13B show various geometries of the support ring.
Figure 13A:
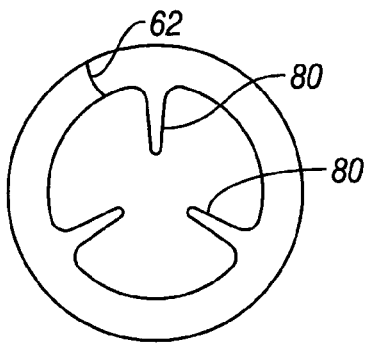
Figure 13B:
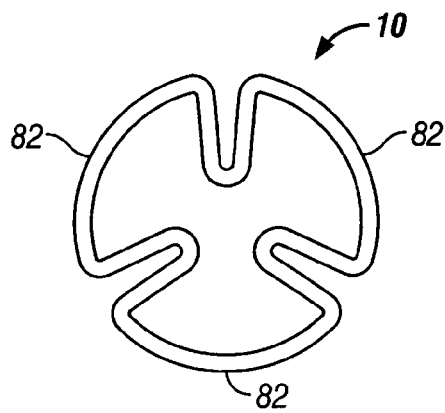

Referring now to FIG. 12, the standard ring-shaped coil device 10 described is only one configuration that may be delivered in a straight configuration and provide support for the valve or target tissue when delivered to its destination. Other shapes may provide additional support for one or more leaflets of the valve or may provide additional support to a damaged portion of the heart valve annulus. For example in FIG. 13A, inner extensions 80 on the ring may provide a backboard for the leaflets preventing prolapse of the valve leaflet during systole of the heart. In another embodiment as seen in FIG. 14B, the ring 12 may be shaped more like a bi-lobed leaf for the mitral valve, or a shamrock or cloverleaf configuration 82 for the three-leaflet tricuspid valve of the heart. The additional inner structure(s) of the cloverleaf configuration 82 provides the valve leaflet with an area that it cannot physically go beyond, ensuring proper coaptation of it and its counterpart leaflet against its corresponding stop on the opposite side of the valve.

Figure 14A:
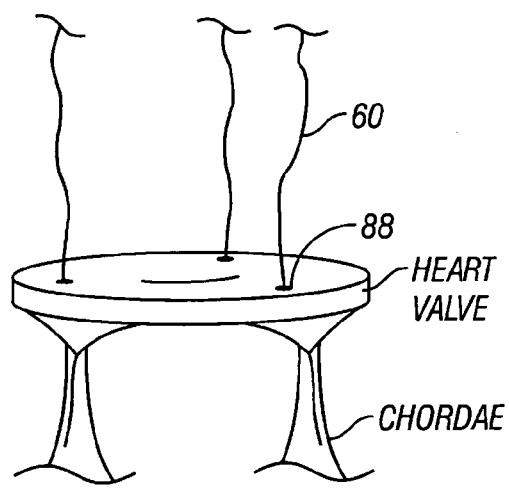
FIGS. 14A–14D illustrate the use of a support ring and sutures at a tissue site.
Figure 14B:
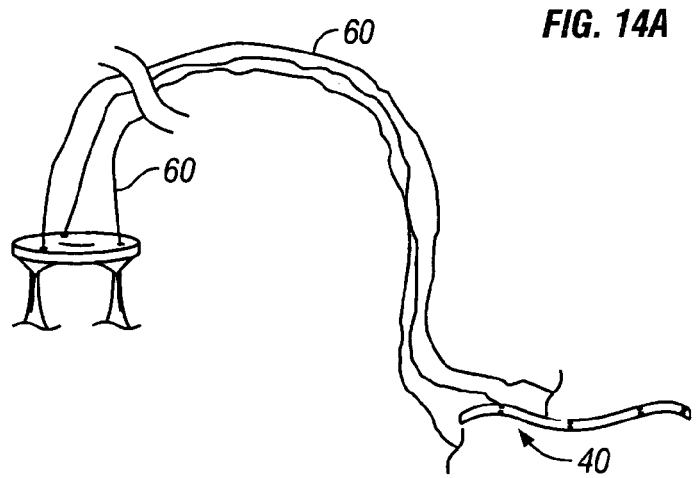

Referring now to FIGS. 14A through 14D, a still further embodiment of the present invention will be described. As seen in FIG. 14A, sutures 60 may be secured to the tissues surrounding the heart valve at anchoring sites 88. The sutures may be secured in a variety of different methods including but not limited to passing sutures through the heart valve material to be looped through or knotted off using a knot pusher. The sutures may also be connected using anchoring devices as described in commonly assigned, copending U.S. Provisional Patent Application Ser. No. 60/388,250 filed Jun. 12, 2002.

Figure 14C:
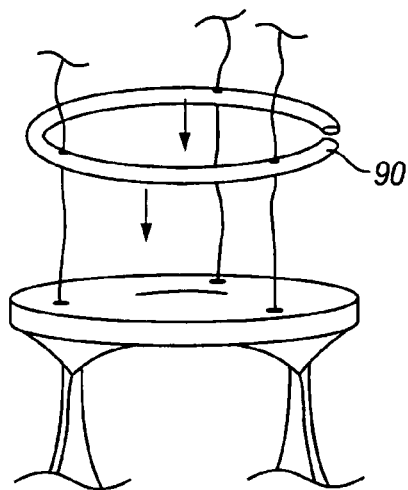
Figure 14D:
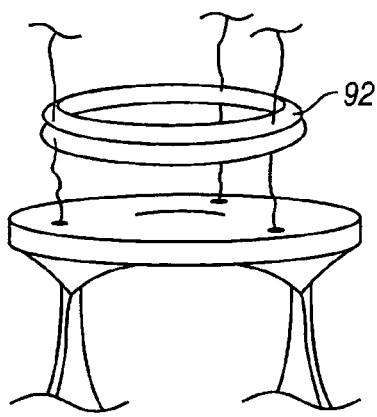

As seen in FIG. 14B, the sutures 60 may then act as guides to advance a slideable tissue supporting member 90 over the sutures to the tissues surrounding the heart valve. In one instance, the supporting member may be of similar size and shape to a conventional annuloplasty ring typically used to repair heart valves during open heart surgery. In one embodiment, the sutures 60 may be of sufficient length to extend from the attachment locations in the valve tissue to outside the body to allow for attachment to device 90. The device 90 may then be slidably advanced over the sutures to the target tissue. This advantageously allows for precise anchoring of the device 90 at the target site. As seen in FIG. 14C, the device 90 may be have a single ring configuration that may be straightened or folded (in other embodiments) to be advanced through a guide catheter to the target site. Alternatively, the device 90 may be a continuous ring without a break, but foldable to be advanced through the guide catheter. As seen in FIG. 14D, a coil ring configuration device 92 may also be used, wherein both coils or rings of the device remain on the same side of the valve tissue. This may allow for additional attachment points on the device 92 or if the coils have varying diameters, different reshaping options based on different angles of the sutures to provide pulling or securing forces in different directions.

In the invention described, the ring may be advanced over the anchored sutures and advanced to the valve through a typical guide catheter. In such a manner, the entire procedure may be performed percutaneously, resulting in less trauma to the patient and providing improved valve function without the need for open heart surgery. After the ring is in position on the valve tissues, each of the locations where the sutures pass through the ring are fastened to the ring using the techniques previously described with clamps and/or knots. Alternatively, it may be possible to secure all of the sutures with a single clamp securing each of the sutures together, as shown in Figure, below.

Figure 15A:
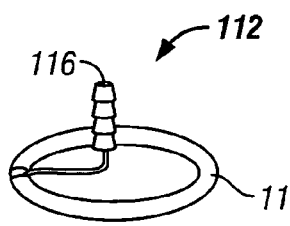
FIGS. 15A–20 show embodiments of the present invention using separable clamping portions.
Figure 15B:
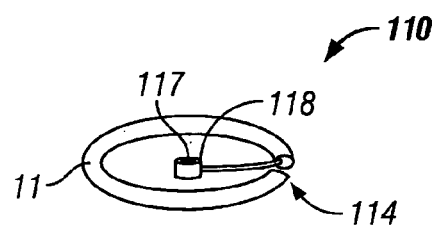

Referring now to FIGS. 15A and 15B, in another embodiment of this invention, the device 110 consists of two separate halves or clamp portions 112 and 114, each of which may provide support for the valve while maintaining a clamping force between them. Clamp portion 112 may have an annular support 113 or leaflet that supports the tissue. Clamp portion 114 may similarly have an annular support 115 or leaflet that supports the tissue. The two clamp portions 112 and 114 are connected to each other via a central adjustable fitting. In one embodiment, the central fitting consists of a barbed connector or spine 116 on one device part that mates to a matching insert 117 on the opposite part with a lumen 118.

Figure 16:
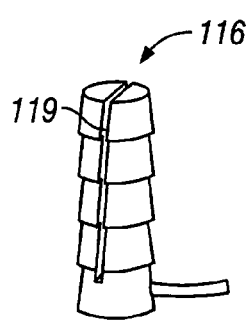

As seen in FIG. 16, the center spine 116 could be split, having a slot 119, to permit the outer diameter of the spine to be adjustable, allowing the distance between the two parts to be adjusted by the physician in-vivo, until the improved function of the heart valve has been observed.

Figure 17:
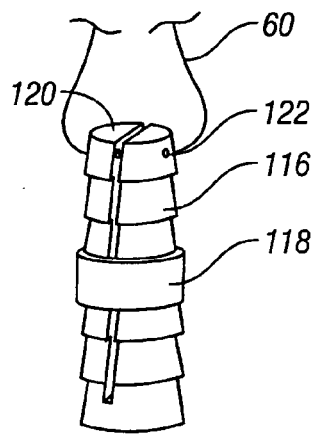
Figure 18:
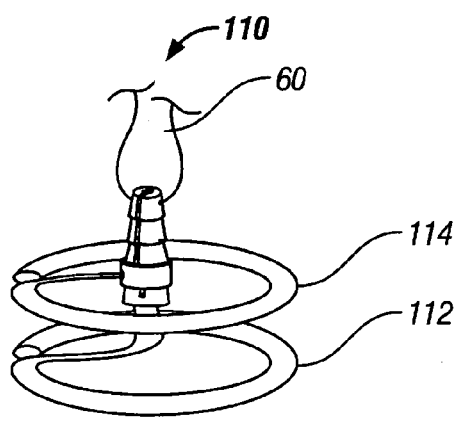

In a further preferred embodiment seen in FIG. 17, the distal end 120 of the center spine 116 may incorporate holes 122 on each half of the barbs. Through the holes 122 is a releasable suture or thread 60 that, when tension is applied, compresses the two halves of the spine 116 together, effectively decreasing its overall outer diameter. This permits the upper half of the device to be adjusted prior to release to allow for more distance between the two halves of the device and less clamping force on the valve area. The complete assembly, including the releasable suture, is illustrated in FIG. 18 (for illustrative purposes, the ring and clamp are shown as simple circular structures). In this manner, the clamping force on the valve and annular support device is entirely controlled by the physician prior to its release in the heart.

Figure 19:
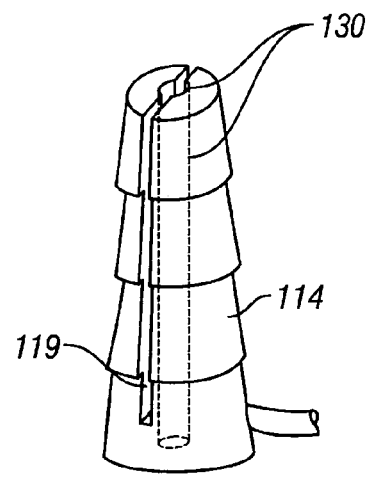

In a further embodiment of the present invention as seen in FIG. 19, the device 110 comprises a lumen 130 through the center spine 116. The lumen 130 provides a space through which a slideable and removable guide wire may be inserted for placement of the device. A matching lumen on the mating half 118 of the device ensures that both pieces remain in the same axis when being delivered. Since both parts of the connector are maintained in axial alignment, securing the devices together is accomplished by pushing the two devices together.

Figure 20:
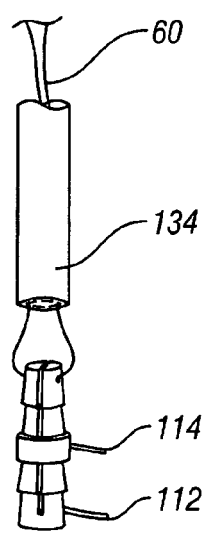

A pushing device 134 of FIG. 20, consisting of a tubular member, allows for tension to be placed on the releasable suture 60 without disrupting the location of the valve support device by holding the center spine in position while tension is applied to the suture. After the desired improvement in valve function has been obtained, the suture is removed by simply releasing one end of the suture and pulling on the other end until the entire suture has been removed from the body. Additionally, other release mechanisms include clamping jaws, screw threads, and other mechanical means, that are releasably connected to the support structure in order to maintain control over the device and to remove the structure from the body if improvement is not realized or for any other reason.

Again, each of the halves 112 and 114 of the device may be hollow allowing for them to be straightened over a mandrel or guide wire for delivery into the valve area. Upon delivery to the valve are, the device(s) are advanced off the removable mandrel/guide wire and they revert back to their pre-determined shape.

In addition to the various coil type annular support rings described above, other types of annuloplasty device may also be used in accordance to the present invention.

Figure 21:
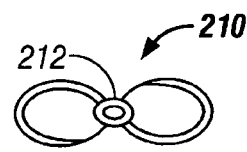
FIGS. 21–27D illustrate varying geometries of leaflet clamps for use with the present invention.
Figure 22:
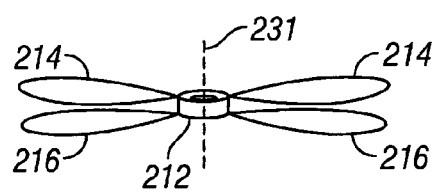

Referring now to FIGS. 21 and 22, in another embodiment of the present invention, a valve support structure 210 is delivered to the valve area via a guide catheter. The device 210 comprises of a central body 212, a first leaflet clamp 214 defining an upper compressive portion, and a second leaflet clamp 216 defining a lower compressive portion. The clamp 212 and clamp 214 may be positioned to engage the valve leaflet therebetween.

Figure 23:
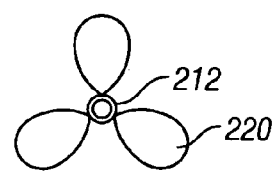

Referring now to FIG. 23, the number of leaflet clamp sets on the device may match the number of leaflets of the valve. For instance, the mitral valve device of this invention may have two sets of clamps. The tricuspid device design may, but is not required to have, three sets of leaflet clamps 220 as seen in FIG. 23. In either instance, the clamps are connected at a central location and radiate outwards towards the valve leaflets.

Figure 24:
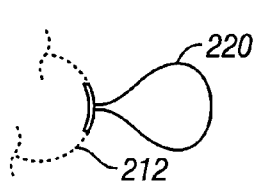
Figure 25:
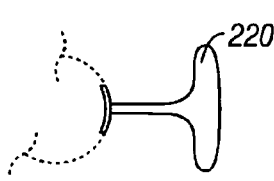
Figure 26:
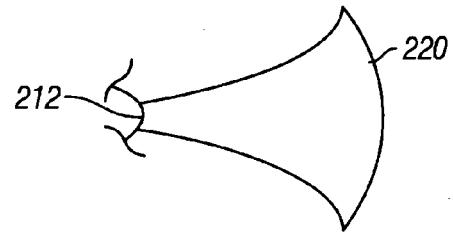

Each leaflet clamp 220 may have a different geometry, depending on the condition of the valve. For instance, if more support is desired at the outer edge of the leaflet, the clamp could have a larger diameter in that area. FIG. 24 shows a wire loop leaflet clamp 220 having a curved configuration where the wire extends radially outward and then returns to the central body 212. FIG. 25 shows an embodiment where the change in width is more pronounced as the wire loop reaches the outer radial portion of the clamp. FIG. 26 shows an embodiment having an oar or paddle configuration. It should be understood that a variety of different geometries may be used to support the leaflet clamps.

Figure 27A:
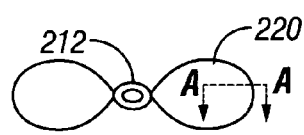
Figure 27B:
Figure 27C:

Referring now to FIGS. 27A–27C, the cross section of the clamp 220 may also have various geometries. For instance, it may be desirable to distribute the clamping force over a larger area, in which case a flattened cross section would be appropriate as seen in FIG. 27B. Alternatively, rounded cross sections may be used in areas where there may need to be increased force on the tissue surface as seen in FIG. 27C.

Figure 27D:
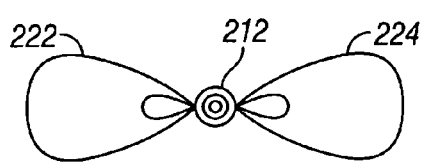

It can be appreciated that there may be any number of configurations for the clamps 214 and 216. For instance, if most of the support for the valve is needed at the area of the annular ring, the clamps may not provide any clamping force on the leaflets themselves, but would be of sufficient overall diameter and distance away from the central hub so as to provide support in the annular area of the valve. Conversely, if a percutaneous procedure yielding similar results to the "bow-tie" procedure is desired, the clamps may be of relatively small outer diameter. In this manner, only the leaflets would be clamped together more central to the device, effectively decreasing the movement of the leaflets, and providing a forced coaptation. Additionally, as seen in FIG. 27D, a combination of both annular support 222 and leaflet coaptation 224 could be achieved in the same device by providing multiple clamps of different diameters to support both the valve leaflets and the valve's annulus.

Figure 28:
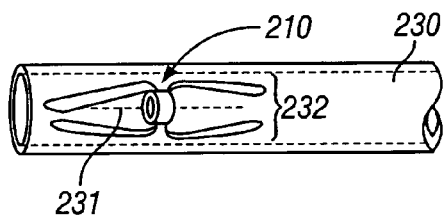
FIGS. 28–30 show the delivery of an apparatus according to the present invention with deflectable leaflet clamps.
Figure 29:
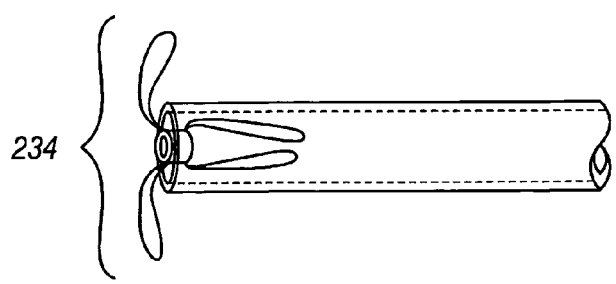
Figure 30:
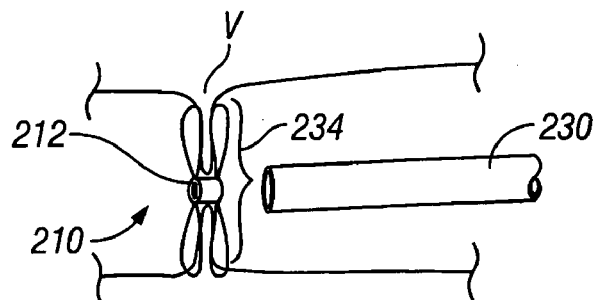

Referring now to FIGS. 28–30, delivery of the device 210 may be achieved through a guide catheter 230. Each of the leaflet clamps 214 and 216 may be made of a superelastic material such as, but not limited to, Nitinol, such that the leaflet clamps 214 and 216 can be folded up into the guide catheter to assume a folded configuration. As seen in FIG. 28, the leaflets clamps are deflected towards a longitudinal axis 231 of the central body to provide a reduced diameter 232 so that the device 210 will fit inside the guide catheter but still assume an expanded configuration with an extended diameter upon exiting the catheter.

As seen in FIGS. 29 and 30, upon release across the heart valve V, the leaflet clamps 214 and 216 return to their functioning state with the extended diameter 234. Alternatively, the device 210 may be made of any one of a number of shape memory alloys, allowing it to be delivered in a straight configuration through the guide catheter, and re-assuming its functioning form following the application of energy in the form of electrical, radio frequency, microwave, and such. In any case, the guide catheter is traversed across the target valve. At the desired location, the device is pushed out the distal end of the guide catheter and upon exiting the guide catheter as seen in FIG. 29, the distal leaflet clamp 214 assumes its clamping dimensions.

The guide catheter 230, still with the proximal leaflet clamps 216 inside in their folded configuration, is then retracted proximally across the valve opening where the remainder of the device 210 is delivered. The leaflet clamp 216 then extends to their preformed configuration with diameter 234, engaging or urging the valve leaflet against the opposing clamp 214 as seen in FIG. 30.

Figure 31:
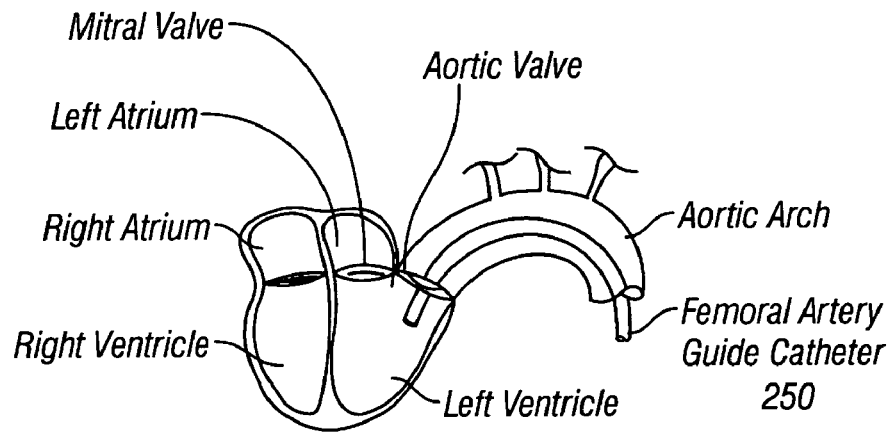
FIGS. 31–35 illustrate positioning of delivery devices to reach a treatment site in the heart.

Referring now to FIGS. 31–35, there are several ways the mitral valve can be accessed percutaneously to deliver the devices described herein, although it should be understood that the devices may be used during open heart surgery as well. As seen in FIG. 31, one route utilizes the femoral artery approach where the guide catheter 250 is threaded through the femoral artery in the groin and advanced retrograde against the flow of blood, over the aortic arch, through the aortic valve, into the left ventricle of the heart, and directed towards the mitral valve.

Figure 32:
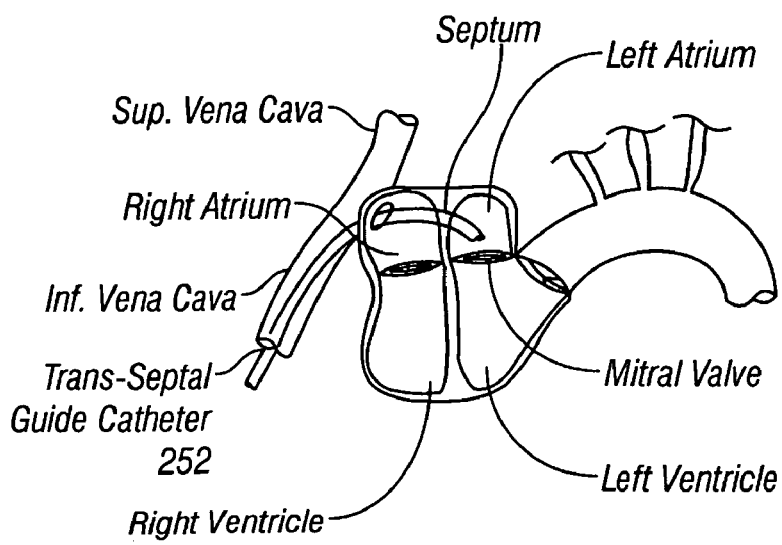

Referring now to FIG. 32, a second approach that may be used during percutaneous valvuloplasty procedures involves the venous approach to the heart. The guide catheter 252 is advanced through the vena cava into the right atrium of the heart and is directed across the atrial septum of the heart into the left atrium of the heart. This approach has been demonstrated to be well-tolerated by the body with few adverse events.

Figure 33:
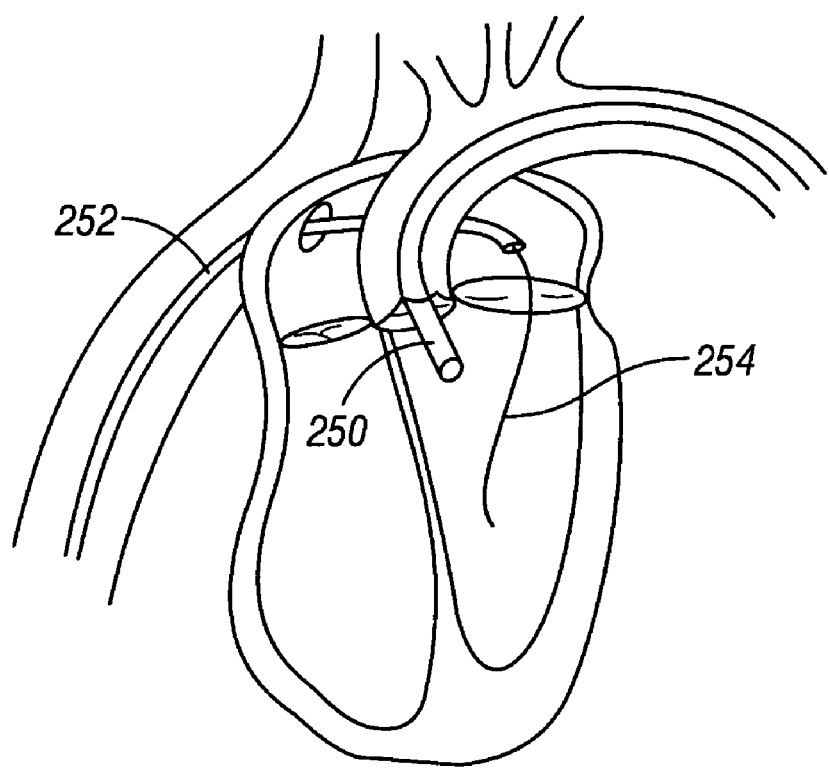
Figure 34:
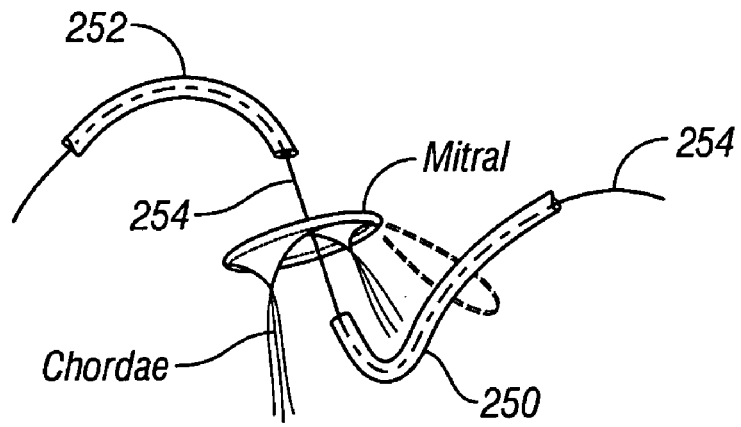

Referring now to FIG. 33, a further method for device placement is described herein that provides unique advantages for devices attempting to modify the performance of the mitral valve percutaneously. First, a trans-septal guide catheter is advanced through the atrial septum of the heart to the superior side of the mitral valve. An extra long guide wire 254, is then advanced through the guide catheter 252 and into the left ventricle. A second guide catheter 250 is advanced to the left ventricle of the heart via the arterial approach. A snare (not shown) may then be advanced through the arterial guide catheter 250 and captures the distal end of the trans-septal guide wire 254. The snare is retracted through the arterial guide catheter 250 where the distal end of the guide wire is captured and secured outside the body. In effect as shown in FIG. 34, the guide wire 254 provides a passage from either or both directions, arterial or venous, to the mitral valve of the heart.

Figure 35:
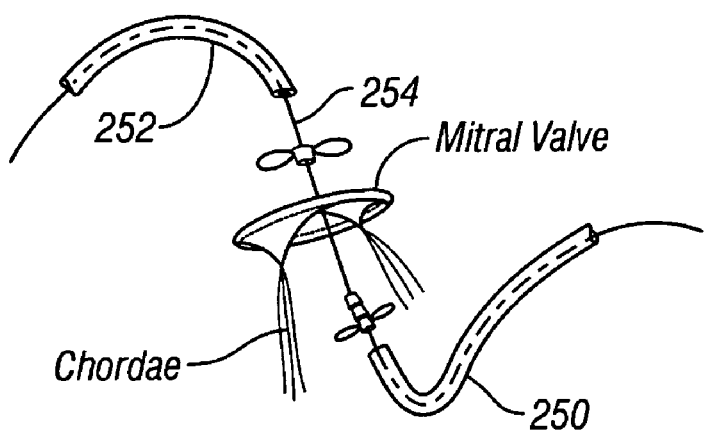

Referring now to FIG. 35, a support ring 114 when threaded over the guide wire from the arterial side need not even cross the mitral valve to provide support to the ventricular side of the valve. Similarly, a second support ring 112 forming device 110 when combined with ring 114, intended to provide support to the atrial side of the mitral valve also need not cross the valve when delivered via the trans-septal route. In this manner, the two halves of mitral valve device 110 can be delivered through the two guide catheters and meet up at the mitral valve. The guide wire 254 additionally ensures that the two mating parts of the device remain in axial alignment when assembled across the valve.

Figure 36:
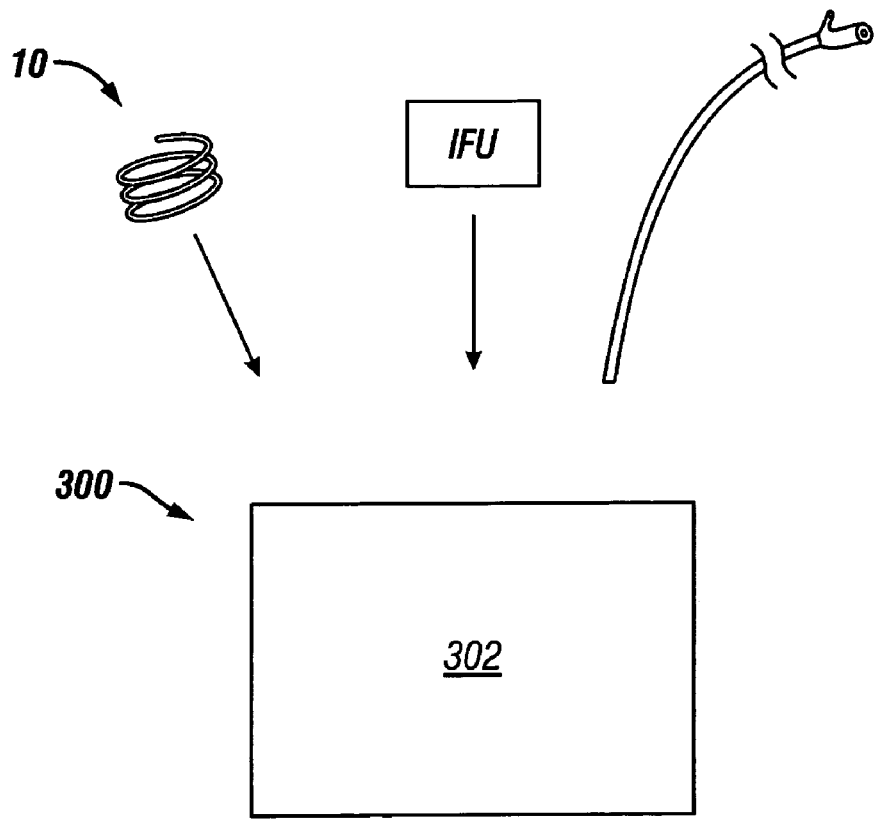
FIG. 36 shows a kit containing an annular support ring and accessories.

Referring now to FIG. 36, the device 10 or any of the other devices 110 or 210 as described herein, may be included in a kit 300 contained in a pouch or container 302. Instructions for use IFU are also contained in or attached to the container 302. The instructions provide a method for using device 10, a method for attaching device 10 to tissue, or instructions on how to deliver device 10 or similar device using a delivery device 20 such as a catheter or straightening mandrel that may also be contained in container 302.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, the geometric configuration of the loops of device 10 or 210 may be varied as desired to provide leaflet support, including shapes such as square, triangular, bowed, rounded, or other configuration. The wire loop elements may also be replaced by solid elements, such as a solid, oar shaped clamp instead of a wire loop. Although device 10 is generally shown to have a circular relaxed configuration, it should also be understood that, in all embodiments, the device may have a square, rectangular, triangular, polygonal, or other shape that will provide suitable reduction of valve regurgitation. Additionally, bringing together tissues in closer proximity to one another is one method for closing wounds such as catheter puncture sites during percutaneous procedures (angioplasty, stenting, endograft procedures and the like), as well as in stomach stapling for the morbidly obese, gastrostomy placement, etc. These procedures all may benefit from the inventions described herein. Additionally, any of the inventions and devices described in this application may be manufactured, at least in part, using animal, human or cultured cells and tissues incorporated in whole or in part. These tissues may be harvested or cultured though tissue engineering or altered by the manipulation of their genetic content. In such a manner, these devices may be incorporated into the target location easier, may be less prone to rejection by the body, or may elude certain chemicals and/or enzymes that may be beneficial to the targeted tissues or the body as a whole. Expected variations or differences in the results are contemplated in accordance with the objects and practices of the present invention. It is intended, therefore, that the invention be defined by the scope of the claims which follow and that such claims be interpreted as broadly as is reasonable.

The invention claimed is:

1. A tissue connecting device for use with an elongate delivery device on tissue at a target site, the device comprising:
   an elongate member deliverable to the target site via the elongate delivery device, said elongate member assuming a first substantially linear configuration while engaged with said delivery device and a second substantially circular configuration defining a first support ring and a second support ring when removed from the delivery device;
   wherein the elongate member has a first support ring radial thickness different from a second support ring radial thickness, said first support ring configured to abut against one side of the target tissue and said second support ring configured to abut against an opposite side of the target tissue to thereby capture a portion of the target tissue therebetween;
   at least one suture coupled to the elongate member; and
   wherein said first support ring is coupled to said second ring via a wire extending radially towards the center of the two rings in a manner sufficient to pass through a non-tissue center of the targeted valve.

2. A tissue connecting device for use with an elongate delivery device on tissue at a target site, the device comprising:
   an elongate member deliverable to the target site via the elongate delivery device, said elongate member assuming a first substantially linear configuration while engaged with said delivery device and a second substantially circular configuration defining a first support ring and a second support ring when removed from the delivery device;
   wherein the elongate member has a first support ring radial thickness different from a second support ring radial thickness, said first support ring configured to abut against one side of the target tissue and said second support ring configured to abut against an opposite side of the target tissue to thereby capture a portion of the target tissue therebetween;
   at least one suture coupled to the elongate member; and
   wherein said delivery device comprises a catheter.

3. A tissue connecting device for use with an elongate delivery device on tissue at a target site, the device comprising:
   an elongate member deliverable to the target site via the elongate delivery device, said elongate member assuming a first substantially linear configuration while engaged with said delivery device and a second substantially circular configuration defining a first support ring and a second support ring when removed from the delivery device;
   wherein the elongate member has a first support ring radial thickness different from a second support ring radial thickness, said first support ring configured to abut against one side of the target tissue and said second support ring configured to abut against an opposite side of the target tissue to thereby capture a portion of the target tissue therebetween at least one detachable suture removably coupled to the elongate member and wherein said first support ring is coupled to said second ring via a wire extending radially towards the center of the two rings in a manner sufficient to pass through a non-tissue center of the targeted valve.

4. A tissue connection device for use with an elongate delivery device and at least one suture on tissue at a treatment site in a patient, the device comprising:
   an elongate member deliverable to a target tissue site via the elongate delivery device, said elongate member assuming a first substantially linear configuration while engaged with the elongate delivery device and a second relaxed configuration defining a first support ring and a second support ring when removed from the elongate delivery device;
   said elongate member in said circular configuration shaped to have a distance between a first ring tissue engaging surface and a second ring tissue engaging surface;
   at least one suture coupled to said elongate member for seating said member against the treatment site; and
   wherein said suture reduces said distance therebetween and increases clamp force on any tissue between said first ring tissue engaging surface and the second ring tissue engaging surface.

5. The device of claim 4 wherein the elongate member is deliverable percutaneously.

6. The device of claim 4 wherein the elongate member has a reduced stiffness wherein said first ring and said second ring reduce valve dilation of tissue therebetween only with use of said suture.

7. The device of claim 4 wherein the elongate member is deliverable to engage a heart valve.

8. The device of claim 4 wherein the first support ring radial thickness greater than said second ring radial thickness.

9. The device of claim 4 wherein at least an outer portion of the first support ring comprises a material selected from one of the following: a nickel titanium alloy, superelastic metallic alloys, superelastic plastic, PTFE, silicone, stainless steel, and ceramic.

10. The device of claim 4 wherein said elongate member comprises a shape-memory material.

11. The device of claim 4 wherein said elongate member comprises a material allowing for penetration by a suture needle to attach a suture therein.

12. The device of claim 4 wherein said elongate member has an outer layer comprising a material allowing for penetration by a suture needle to attach a suture therein.

13. The device of claim 4 further comprising a plurality of apertures on said first ring sufficient for attachment of sutures to the first ring.

14. The device of claim 4 wherein first support ring has a surface suitable for engagement by sutures.

15. The device of claim 4 wherein said elongate member comprises a material suitable for penetration by sutures.

16. The device of claim 4 wherein first support ring has a mesh cover.

17. The device of claim 4 wherein the first support ring has a Dacron® covering.

18. The device of claim 4 further comprising a plurality of anchoring locations on said first support ring sufficient to allow for attachment of sutures to the first ring.

19. The device of claim 4 further comprising at least one suture coupled to the elongate member.

20. The device of claim 4 further comprising at least one detachable suture removably coupled to the elongate member.

21. The device of claim 4 wherein said elongate member includes at least one radiopaque marker.

22. The device of claim 4 wherein said distal end is spaced apart from said proximal end when said elongate member is in the first, substantially linear configuration.

23. The device of claim 4 wherein said first support ring and said second support ring define an overlapping coil configuration.

24. The device of claim 23 wherein said first support ring is configured to engage an inner circumferential surface of the second support ring.

25. The device of claim 4 wherein said first support ring is in a plane parallel to a second support ring plane.

26. The device of claim 4 wherein said elongate member is configured to connect the first ring to the second ring without penetrating said target tissue.

27. The device of claim 4 wherein said delivery device comprises a catheter.

28. A tissue connection device for use with an elongate delivery device and at least one suture on tissue at a treatment site in a patient, the device comprising:

an elongate member deliverable to a target tissue site via the elongate delivery device, said elongate member assuming a first substantially linear configuration while engaged with the elongate delivery device and a second relaxed configuration defining a first support ring and a second support ring when removed from the elongate delivery device;

said elongate member in said circular configuration shaped to have a distance between a first ring tissue engaging surface and a second ring tissue engaging surface;

at least one suture coupled to said elongate member for seating said member against the treatment site; and wherein the elongate member has a reduced stiffness wherein said first ring and said second ring reduce valve dilation of tissue therebetween only with use of said suture.

29. The device of claim 28 wherein said suture reduces said distance therebetween and increases clamp force on any tissue between said first ring tissue engaging surface and the second ring tissue engaging surface.

30. The device of claim 28 wherein the elongate member is deliverable percutaneously.

31. The device of claim 28 wherein the elongate member is deliverable to engage a heart valve.

32. The device of claim 28 wherein the first support ring radial thickness greater than said second ring radial thickness.

33. The device of claim 28 wherein at least an outer portion of the first support ring comprises a material selected from one of the following: a nickel titanium alloy, superelastic metallic alloys, superelastic plastic; PTFE, silicone, stainless steel, and ceramic.

34. The device of claim 28 wherein said elongate member comprises a shape-memory material.

35. The device of claim 28 wherein said elongate member comprises a material allowing for penetration by a suture needle to attach a suture therein.

36. The device of claim 28 wherein said elongate member has an outer layer comprising a material allowing for penetration by a suture needle to attach a suture therein.

37. The device of claim 28 further comprising a plurality of apertures on said first ring sufficient for attachment of sutures to the first ring.

38. The device of claim 28 wherein first support ring has a surface suitable for engagement by sutures.

39. The device of claim 28 wherein said elongate member comprises a material suitable for penetration by sutures.

40. The device of claim 28 wherein first support ring has a mesh cover.

41. The device of claim 28 wherein the first support ring has a Dacron® covering.

42. The device of claim 28 further comprising a plurality of anchoring locations on said first support ring sufficient to allow for attachment of sutures to the first ring.

43. The device of claim 28 further comprising at least one suture coupled to the elongate member.

44. The device of claim 28 further comprising at least one detachable suture removably coupled to the elongate member.

45. The device of claim 28 wherein said elongate member includes at least one radiopaque marker.

46. The device of claim 28 wherein said distal end is spaced apart from said proximal end when said elongate member is in the first, substantially linear configuration.

47. The device of claim 28 wherein said first support ring and said second support ring define an overlapping coil configuration.

48. The device of claim 47 wherein said first support ring is configured to engage an inner circumferential surface of the second support ring.

49. The device of claim 28 wherein said first support ring is in a plane parallel to a second support ring plane.

50. The device of claim 28 wherein said elongate member is configured to connect the first ring to the second ring without penetrating said target tissue.

51. The device of claim 28 wherein said delivery device comprises a catheter.

52. A tissue connection device for use with an elongate delivery device and at least one suture on tissue at a treatment site in a patient, the device comprising:

an elongate member deliverable to a target tissue site via the elongate delivery device, said elongate member assuming a first substantially linear configuration while engaged with the elongate delivery device and a second relaxed configuration defining a first support ring and a second support ring when removed from the elongate delivery device;

said elongate member in said circular configuration shaped to have a distance between a first ring tissue engaging surface and a second ring tissue engaging surface;

at least one suture coupled to said elongate member for seating said member against the treatment site; and a plurality of apertures on said first ring sufficient for attachment of sutures to the first support ring.

53. The device of claim 52 wherein said suture reduces said distance therebetween and increases clamp force on any tissue between said first ring tissue engaging surface and the second ring tissue engaging surface.

54. The device of claim 52 wherein the elongate member is deliverable percutaneously.

55. The device of claim 52 wherein the elongate member has a reduced stiffness wherein said first ring and said second ring reduce valve dilation of tissue therebetween only with use of said suture.

56. The device of claim 52 wherein the elongate member is deliverable to engage a heart valve.

57. The device of claim 52 wherein the first support ring radial thickness greater than said second ring radial thickness.

58. The device of claim 52 wherein at least an outer portion of the first support ring comprises a material selected from one of the following: a nickel titanium alloy, superelastic metallic alloys, superelastic plastic, PTFE, silicone, stainless steel, and ceramic.

59. The device of claim 52 wherein said elongate member comprises a shape-memory material.

60. The device of claim 52 wherein said elongate member comprises a material allowing for penetration by a suture needle to attach a suture therein.

61. The device of claim 52 wherein said elongate member has an outer layer comprising a material allowing for penetration by a suture needle to attach a suture therein.

62. The device of claim 52 wherein first support ring has a surface suitable for engagement by sutures.

63. The device of claim 52 wherein said elongate member comprises a material suitable for penetration by sutures.

64. The device of claim 52 wherein first support ring has a mesh cover.

65. The device of claim 52 wherein the first support ring has a Dacron® covering.

66. The device of claim 52 further comprising a plurality of anchoring locations on said first support ring sufficient to allow for attachment of sutures to the first ring.

67. The device of claim 52 further comprising at least one suture coupled to the elongate member.

68. The device of claim 52 further comprising at least one detachable suture removably coupled to the elongate member.

69. The device of claim 52 wherein said elongate member includes at least one radiopaque marker.

70. The device of claim 52 wherein said distal end is spaced apart from said proximal end when said elongate member is in the first, substantially linear configuration.

71. The device of claim 52 wherein said first support ring and said second support ring define an overlapping coil configuration.

72. The device of claim 71 wherein said first support ring is configured to engage an inner circumferential surface of the second support ring.

73. The device of claim 52 wherein said first support ring is in a plane parallel to a second support ring plane.

74. The device of claim 52 wherein said elongate member is configured to connect the first ring to the second ring without penetrating said target tissue.

75. The device of claim 52 wherein said first support ring is coupled to said second ring via a wire extending radially towards the center of the two rings in a manner sufficient to pass through a non-tissue center of the targeted valve.

76. The device of claim 52 wherein said elongate member is configured to connect the first ring to the second ring without penetrating said target tissue.

77. The device of claim 52 wherein said delivery device comprises a catheter.

78. A tissue connection device for use with an elongate delivery device and at least one suture on tissue at a treatment site in a patient, the device comprising:

an elongate member deliverable to a target tissue site via the elongate delivery device, said elongate member assuming a first substantially linear configuration while engaged with the elongate delivery device and a second relaxed configuration defining a first support ring and a second support ring when removed from the elongate delivery device;

said elongate member in said circular configuration shaped to have a distance between a first ring tissue engaging surface and a second ring tissue engaging surface;

at least one suture coupled to said elongate member for seating said member against the treatment site;

at least one detachable suture removably coupled to the elongate member; and a plurality of apertures on said first ring sufficient for attachment of sutures to the first ring.

79. A tissue connection device for use with an elongate delivery device and at least one suture on tissue at a treatment site in a patient, the device comprising:

an elongate member deliverable to a target tissue site via the elongate delivery device, said elongate member assuming first substantially linear configuration while engaged with the elongate delivery device and a second relaxed configuration defining a first support ring and a second support ring when removed from the elongate delivery device;

said elongate member in said circular configuration shaped to have a distance between a first ring tissue engaging surface and a second ring tissue engaging surface;

at least one suture coupled to said elongate member for seating said member against the treatment site; at least one detachable suture removably coupled to the elongate member; and wherein said first support ring is coupled to said second ring via a wire extending radially towards the center of the two rings in a manner sufficient to pass through a non-tissue center of the targeted valve.

* * * * *